US011638538B2

(12) United States Patent
Guibene et al.

(10) Patent No.: US 11,638,538 B2
(45) Date of Patent: May 2, 2023

(54) METHODS AND APPARATUS FOR FALL PREVENTION

(71) Applicant: Charter Communications Operating, LLC, St. Louis, MO (US)

(72) Inventors: Wael Guibene, Denver, CO (US); Muhammad Khan, Greenwood Village, CO (US); Hossam Hmimy, Aurora, CO (US)

(73) Assignee: Charter Communications Operating, LLC, St. Louis, MO (US)

( * ) Notice: Subject to any disclaimer, the term of this patent is extended or adjusted under 35 U.S.C. 154(b) by 541 days.

(21) Appl. No.: 16/806,390

(22) Filed: Mar. 2, 2020

(65) Prior Publication Data

US 2021/0267491 A1   Sep. 2, 2021

(51) Int. Cl.
| | | |
|---|---|---|
| *A61B 5/11* | (2006.01) | |
| *G06N 3/08* | (2023.01) | |
| *G06V 10/764* | (2022.01) | |
| *G06V 40/20* | (2022.01) | |
| *G06V 10/774* | (2022.01) | |

(Continued)

(52) U.S. Cl.
CPC .......... *A61B 5/1117* (2013.01); *A61B 5/1128* (2013.01); *G06N 3/08* (2013.01); *G06V 10/764* (2022.01); *G06V 10/774* (2022.01); *G06V 10/82* (2022.01); *G06V 10/95* (2022.01); *G06V 40/103* (2022.01); *G06V 40/23* (2022.01); *G06T 2207/20084* (2013.01)

(58) Field of Classification Search
CPC .................... G06V 20/52; G06V 40/23; G06T 2207/30232; A61B 5/002; A61B 5/0022
See application file for complete search history.

(56) References Cited

U.S. PATENT DOCUMENTS

| | | | | |
|---|---|---|---|---|
| 2010/0049095 A1* | 2/2010 | Bunn | ..................... | G16H 40/60 600/595 |
| 2013/0127620 A1* | 5/2013 | Siebers | ................. | A61B 5/1113 340/573.1 |

(Continued)

FOREIGN PATENT DOCUMENTS

| | | |
|---|---|---|
| WO | 2011016782 A1 | 2/2011 |
| WO | 2019096783 A1 | 5/2019 |

*Primary Examiner* — Amandeep Saini
*Assistant Examiner* — Raphael Schwartz
(74) *Attorney, Agent, or Firm* — Young Basile Hanlon & MacFarlane, P.C.

(57) ABSTRACT

A system for fall prevention includes a platform for supporting a patient, the platform including rails and rail sensors, an image capturing device for capturing images of the patient, a patient monitor for interactive communication with the patient, a health monitoring station for receiving rail sensor data and communicating with the patient monitor, and an edge network device co-located with the platform and communicating with the station and the image capturing device. The edge network device receives image data from the image capturing device when the rail sensors indicate that the rail is down and the patient is at risk to themselves, anonymizes the image data to generate a skeleton image, determines a posture associated with the skeleton image, triggers alerts at the station when the patient is predicted to be sitting, and triggers escalated alerts at the station when the patient is predicted to be standing.

15 Claims, 8 Drawing Sheets

(51) Int. Cl.
    *G06V 10/82*     (2022.01)
    *G06V 10/94*     (2022.01)
    *G06V 40/10*     (2022.01)

(56) References Cited

U.S. PATENT DOCUMENTS

| | | | |
|---|---|---|---|
| 2015/0109442 A1* | 4/2015 | Derenne | H04N 7/185 |
| | | | 348/143 |
| 2016/0147959 A1 | 5/2016 | Mariottini et al. | |
| 2019/0294871 A1* | 9/2019 | Vaezi Joze | G06N 3/08 |
| 2019/0385430 A1 | 12/2019 | Criado-Perez et al. | |

* cited by examiner

FIG. 5A Curve of training loss.

FIG. 5B Curve of training accuracy.

METHODS AND APPARATUS FOR FALL PREVENTION

TECHNICAL FIELD

This disclosure relates to patient care monitoring. More specifically, this disclosure relates to non-intrusive determining of a posture status of a patient.

BACKGROUND

Falls in hospitals, nursing homes, rehabilitation centers, and other medical facilities are a common problem. This is especially true for medicated, elderly, and similarly situated patients. These falls can result in injuries such as fractures, head trauma, and the like. At the very least, these falls can result in discomfort for the patients and possible aggravation of existing issues or conditions. Present methods for addressing these concerns are costly, inefficient, or take a long time to implement, and include, for example, assigning nurses to check up on patients regularly, having a family member sit in with the patient, educating patients on when, how and where to walk if needed, reducing medication, which is not always possible, and installing costly hand-rails along walk paths.

SUMMARY

Disclosed herein are methods, apparatus, and systems for fall prevention.

In implementations, a system for fall prevention includes a platform configured to support a patient, the platform including rails and rail sensors, an image capturing device configured to capture images of at least the patient, a patient monitor configured for interactive communication with the patient, a health monitoring station configured to receive rail sensor data and in communication with the patient monitor, and an edge network device co-located with the platform and in communication with the health monitoring station and the image capturing device. The edge network device configured to receive image data from the image capturing device when the rail sensors indicate that the rail is down and the patient is at risk to themselves, anonymize the image data to generate a skeleton image, determine a posture associated with the skeleton image, trigger alerts at the health monitoring station when the patient is predicted to be sitting instead of lying down on the platform, and trigger escalated alerts at the health monitoring station when the patient is predicted to be standing instead of lying down on the platform.

BRIEF DESCRIPTION OF THE DRAWINGS

The disclosure is best understood from the following detailed description when read in conjunction with the accompanying drawings. It is emphasized that, according to common practice, the various features of the drawings are not to scale. On the contrary, the dimensions of the various features are arbitrarily expanded or reduced for clarity.

DETAILED DESCRIPTION

Reference will now be made in greater detail to embodiments of the invention, examples of which are illustrated in the accompanying drawings. Wherever possible, the same reference numerals will be used throughout the drawings and the description to refer to the same or like parts.

As used herein, the terminology "computer" or "computing device" includes any unit, or combination of units, capable of performing any method, or any portion or portions thereof, disclosed herein.

As used herein, the terminology "processor" indicates one or more processors, such as one or more special purpose processors, one or more digital signal processors, one or more microprocessors, one or more controllers, one or more microcontrollers, one or more application processors, one or more central processing units (CPU)s, one or more graphics processing units (GPU)s, one or more digital signal processors (DSP)s, one or more application specific integrated circuits (ASIC)s, one or more application specific standard products, one or more field programmable gate arrays, any other type or combination of integrated circuits, one or more state machines, or any combination thereof.

As used herein, the terminology "memory" indicates any computer-usable or computer-readable medium or device that can tangibly contain, store, communicate, or transport any signal or information that may be used by or in connection with any processor. For example, a memory may be one or more read-only memories (ROM), one or more random access memories (RAM), one or more registers, low power double data rate (LPDDR) memories, one or more cache memories, one or more semiconductor memory devices, one or more magnetic media, one or more optical media, one or more magneto-optical media, or any combination thereof.

As used herein, the terminology "instructions" may include directions or expressions for performing any method, or any portion or portions thereof, disclosed herein, and may be realized in hardware, software, or any combination thereof. For example, instructions may be implemented as information, such as a computer program, stored in memory that may be executed by a processor to perform any of the respective methods, algorithms, aspects, or combinations thereof, as described herein. Instructions, or a portion thereof, may be implemented as a special purpose processor, or circuitry, that may include specialized hardware for carrying out any of the methods, algorithms, aspects, or combinations thereof, as described herein. In some implementations, portions of the instructions may be distributed across multiple processors on a single device, on multiple devices, which may communicate directly or across a network such as a local area network, a wide area network, the Internet, or a combination thereof.

As used herein, the term "application" refers generally to a unit of executable software that implements or performs one or more functions, tasks or activities. For example, applications may perform one or more functions including, but not limited to, telephony, web browsers, e-commerce transactions, media players, travel scheduling and management, smart home management, entertainment, and the like. The unit of executable software generally runs in a predetermined environment and/or a processor.

As used herein, the terminology "determine" and "identify," or any variations thereof includes selecting, ascertaining, computing, looking up, receiving, determining, establishing, obtaining, or otherwise identifying or determining in any manner whatsoever using one or more of the devices and methods are shown and described herein.

As used herein, the terminology "example," "the embodiment," "implementation," "aspect," "feature," or "element" indicates serving as an example, instance, or illustration. Unless expressly indicated, any example, embodiment, implementation, aspect, feature, or element is independent of each other example, embodiment, implementation, aspect, feature, or element and may be used in combination with any other example, embodiment, implementation, aspect, feature, or element.

As used herein, the terminology "or" is intended to mean an inclusive "or" rather than an exclusive "or." That is unless specified otherwise, or clear from context, "X includes A or B" is intended to indicate any of the natural inclusive permutations. That is if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from the context to be directed to a singular form.

Further, for simplicity of explanation, although the figures and descriptions herein may include sequences or series of steps or stages, elements of the methods disclosed herein may occur in various orders or concurrently. Additionally, elements of the methods disclosed herein may occur with other elements not explicitly presented and described herein. Furthermore, not all elements of the methods described herein may be required to implement a method in accordance with this disclosure. Although aspects, features, and elements are described herein in particular combinations, each aspect, feature, or element may be used independently or in various combinations with or without other aspects, features, and elements.

Further, the figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical similar devices, systems, compositions and methods. Those of ordinary skill may thus recognize that other elements and/or steps may be desirable or necessary to implement the devices, systems, compositions and methods described herein. However, because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art in light of the discussion herein.

Described herein are methods, apparatus, and systems for fall prevention. The described techniques are proactive measures which attempt to prevent falls as opposed to reactive measures which detect and react to a fall. In particular, the fall prevention techniques track a posture status of a patient by using anonymized patient images which are classified via machine learning algorithms. Different levels of patient alerts are generated depending on a health status and the posture status of the patient.

In implementations, rooms in hospitals, nursing homes, rehabilitation centers, and other medical facilities are provided with a variety of sensors to capture patient data and equipment data. The sensors can include video cameras, bedrail sensors, patient wearables, and the like. In implementations, the bedrail sensors, patient wearables, and the like are connected to a gateway or like network device, which in turn sends the collected sensor data to a health monitoring station. In implementations, the video cameras and the like are connected to an edge gateway or like network device. Image data from the video cameras are anonymized and posture data is extracted and classified. Classification of the posture data determines whether the patient is lying in bed, sitting, or standing.

In an implementation, the captured image data undergoes image processing and a skeleton image is generated which includes body, hand, facial, and foot keypoints or bone nodes. A trained posture detection convolutional neural network (CNN) performs posture classification on the skeleton image. A series of escalating alerts can be used based on a condition of the patient. For patients with a high degree of risk, immediate intervention can be performed to prevent a fall if the posture classification indicates the patient is in a sitting position. This may include verbal communications using a patient bedside monitoring assistant. In implementations, alert escalation can be triggered if the patient is not responsive to the verbal communications or further monitoring and posture classifications indicate that the patient is now standing. This may result in alerting medical personnel to go the patient's room, for example.

Figure 1:
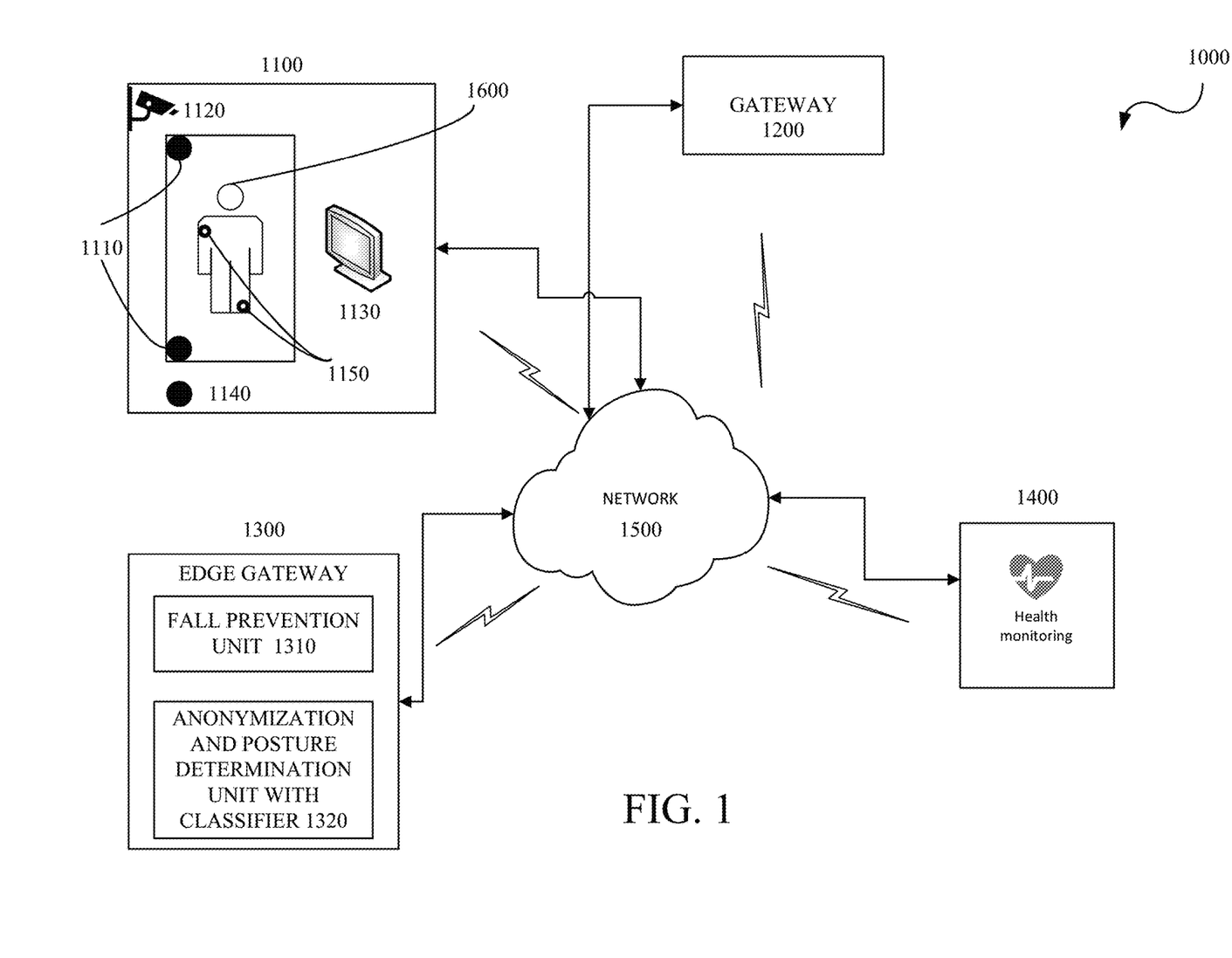
FIG. 1 is a diagram of an example architecture in accordance with embodiments of this disclosure.

FIG. 1 is a diagram of an example architecture or system 1000 in accordance with some embodiments of this disclosure. In implementations, the architecture or system 1000 can be deployed, provided, or implemented in hospitals, nursing homes, rehabilitation centers, and other medical facilities. In an implementation, the architecture 1000 can include one or more patient rooms 1100, a gateway or network device 1200, an edge gateway or network device 1300, a health monitoring personnel station 1400, and a network 1500. The edge gateway 1300 can include a fall prevention unit 1310 and an anonymization and posture determination unit and classifier 1320. In implementations, the fall prevention unit 1310 and the anonymization and posture determination unit and classifier 1320 are integrated. The gateway 1200, the edge gateway 1300, the health monitoring personnel station 1400, and the one or more patient rooms 1100 can be connected to or be in communication with (collectively "connected to") each other using one or more wired or wireless networks of the network 1500. In implementations, the gateway 1200 and the edge gateway 1300 can be one gateway. The architecture 1000 may include other elements which may be desirable or necessary to implement the devices, systems, compositions and methods described herein. However, because such elements and steps are well known in the art, and because they do not facilitate a better understanding of the disclosed embodiments, a discussion of such elements and steps may not be provided herein.

The network 1500 may be, but is not limited to, the Internet, an intranet, a low power wide area network (LP-WAN), a local area network (LAN), a wide area network (WAN), a public network, a private network, a cellular network, a WiFi-based network, a telephone network, a landline network, public switched telephone network (PSTN), a wireless network, a wired network, a private branch exchange (PBX), an Integrated Services Digital Network (ISDN), a IP Multimedia Services (IMS) network, a Voice over Internet Protocol (VoIP) network, and the like including any combinations thereof.

The one or more patient rooms 1100 can each include bedrail sensors 1110, a video camera 1120, a bedside patient monitor 1130, and one or more room sensors 1140. A patient 1600 occupying the patient room 1100 can have one or more wearable health sensors 1150. In implementations, the bedrail sensors 1110 can detect when the bedrail is up (engaged) or down (disengaged). In implementations, the room sensors 1140 can detect the presence of a patient in the one or more patient rooms 1100, a room temperature, other building conditions such as fire, smoke, and the like. In implementations, the one or more wearable health sensors 1150 can be wireless wearable sensors. In implementations, the one or more wearable health sensors 1150 can wrist devices, chests devices, and the like. In implementations, the one or more wearable health sensors 1150 can measure heart beats or rate, temperature, blood pressure, oxygen levels, and other physiological attributes or measurements. In implementations, the video camera 1120 can capture videos and image data of the patient 1600. In implementations, capturing of the videos and image data is triggered when the bedrail sensors 1110 detect that the bedrail is down (disengaged).

The bedside patient monitor 1130 can be smart monitors, smartphones, computers, desktop computers, handheld computers, PDAs, personal media devices, notebooks, notepads, phablets and the like which can communicate between a patient in the one or more patient rooms 1100 and the health monitoring personnel station 1400 using, for example, the network 1500. In implementations, the patient 1600 can communicate using verbal commands, tactile input, audio/visual (AV) applications, and the like to trigger actions at the health monitoring personnel station 1400 including, for example, requesting water, medicine, watching TV, or calling medical personnel.

The gateway 1200 may be a router, gateway device, modem, and like device which provides connectivity including Internet connectivity, wired connectivity, wireless connectivity, and combinations thereof. The gateway 1200 can receive sensor readings from the bedrail sensors 1110, the room sensors 1140, and the one or more wearable health monitors 1150 and transmit the sensor readings to the health monitoring personnel station 1400. In implementations, the sensor readings are received using a LPWAN protocol.

The edge gateway 1300 may be a router, gateway device, modem, and like device which provides connectivity including Internet connectivity, wired connectivity, wireless connectivity, and combinations thereof. The edge gateway 1300 can receive captured video and/or images from the video camera 1120. The anonymization and posture determination unit 1320 can anonymize the captured video and/or images, determine a patient posture, and classify the patient posture as described herein. The fall prevention unit 1310 can use the sensor readings from the bedrail sensors 1110, the detected patient posture, and a patient condition to determine what actions are needed to prevent a fall. In implementations, the edge gateway 1300 can communicate information received from the bedside patient monitor 1130 to the health monitoring personnel station 1400 via the network 1500. In implementations, the edge gateway 1300 is located in the one or more patient rooms 1100.

The health monitoring personnel station 1400 can include smart monitors, smartphones, computers, desktop computers, handheld computers, PDAs, personal media devices, notebooks, notepads, phablets and the like which provide alerts, communication interfaces to the one or more patient rooms 1100 via the bedside patient monitor 1130, for example, and the like. In implementations, the health monitoring personnel station 1400 includes dashboards for real-time monitoring of the one or more patient rooms 1100 and audible or visual indicators and/or alerts if the bedrail is down, for example. In implementations, the communications can be done using a lightweight messaging protocol such as MQTT, for example.

Figure 2A:
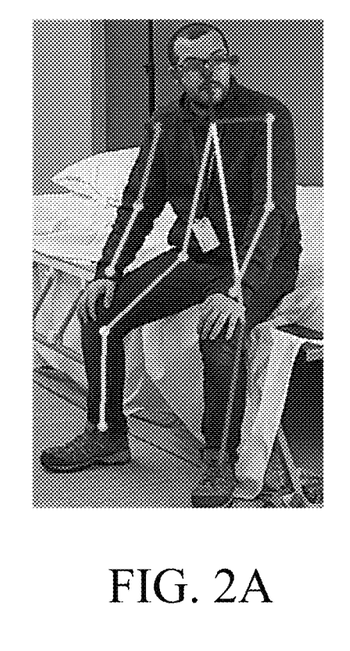
FIG. 2A is an image of a person in a sitting position and FIG. 2B is a skeleton image of the image of FIG. 2A in accordance with embodiments of this disclosure.
Figure 2B:
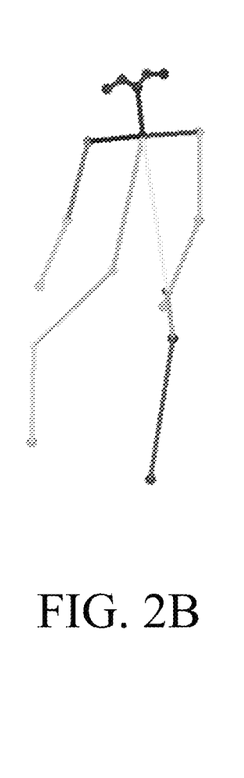
Figure 2C:
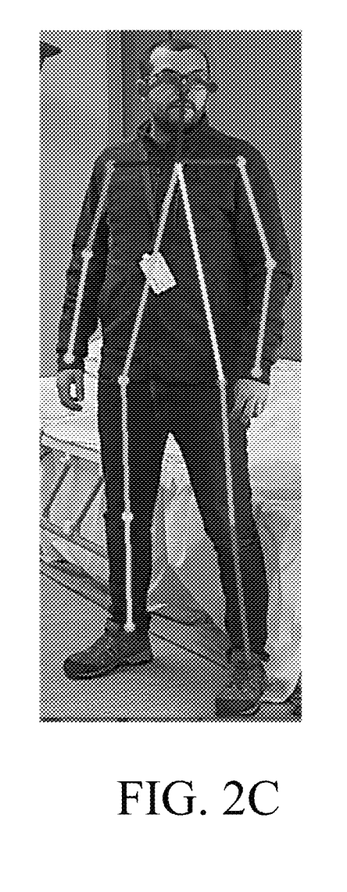
FIG. 2C is an image of a person in a standing position and FIG. 2D is a skeleton image of the image of FIG. 2C in accordance with embodiments of this disclosure.
Figure 2D:
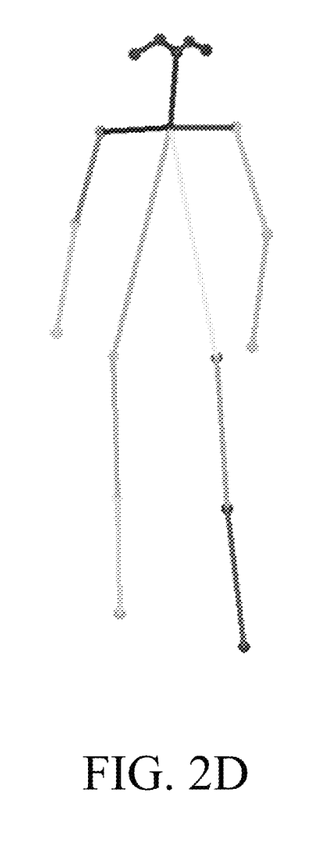
Figure 3A:
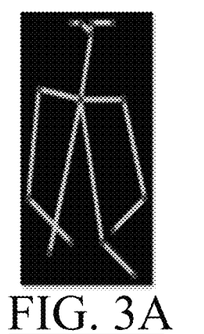
FIGS. 3A-3J are extracted feature maps with patient bone nodes in accordance with embodiments of this disclosure.
Figure 3B:
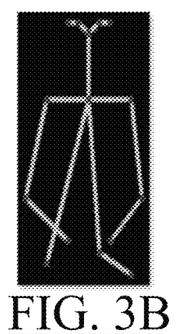
Figure 3C:
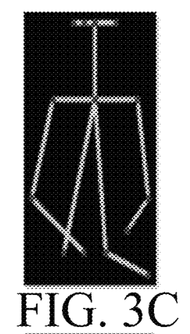
Figure 3D:
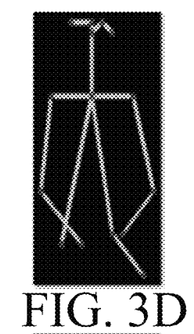
Figure 3E:
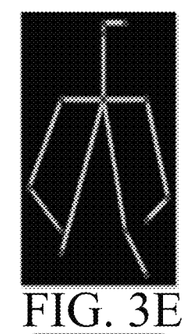
Figure 3F:
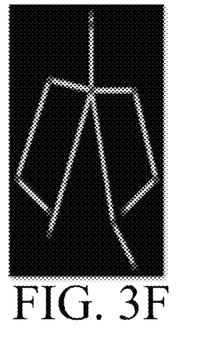
Figure 3G:
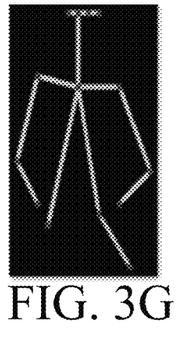
Figure 3H:
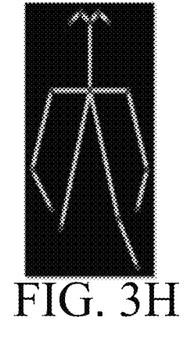
Figure 3I:
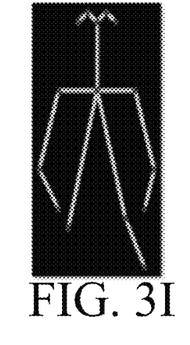
Figure 3J:
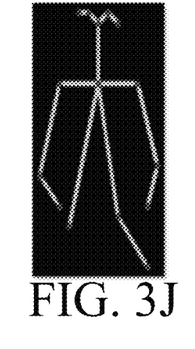

The anonymization and posture determination unit 1320 is a non-intrusive and anonymous technique for determining a posture of a patient. In implementations, anonymity of the patient is maintained by not storing or transmitting the original captured video and/or images beyond the edge gateway 1300. The anonymization and posture determination unit 1320 generates a skeleton image from the captured images. FIG. 2A is an image of a person in a sitting position and FIG. 2B is a skeleton image of the image of FIG. 2A in accordance with embodiments of this disclosure. FIG. 2C is an image of a person in a standing position and FIG. 2D is a skeleton image of the image of FIG. 2C in accordance with embodiments of this disclosure. In implementations, Open-Pose can be used to determine human body, hand, facial, and foot keypoints or bone nodes from the captured images and extract the sitting posture characteristics of the patient. As described with respect to FIG. 4, the extracted feature maps marked with the patient bone nodes are used as a training dataset for building a posture model and/or classifier 1322. For example, a set of feature maps marked with the patient bone nodes are shown in FIGS. 3A-J. The anonymization and posture determination unit 1320 inputs the skeleton image of the patient image into the posture model and/or classifier 1322 and derives the patient posture.

Figure 4:
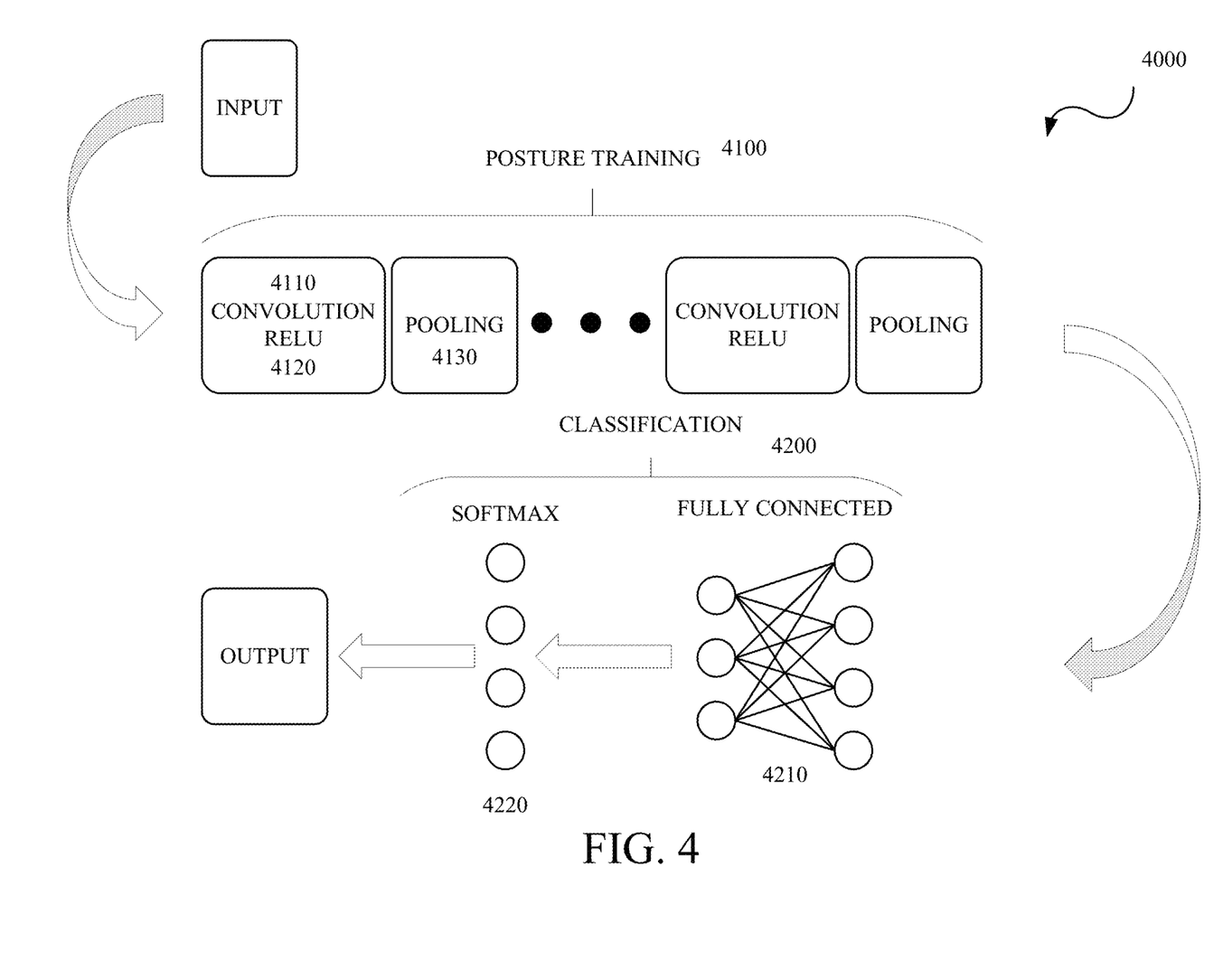
FIG. 4 is a block diagram of an example framework for posture determination in accordance with embodiments of this disclosure.
Figure 5A:
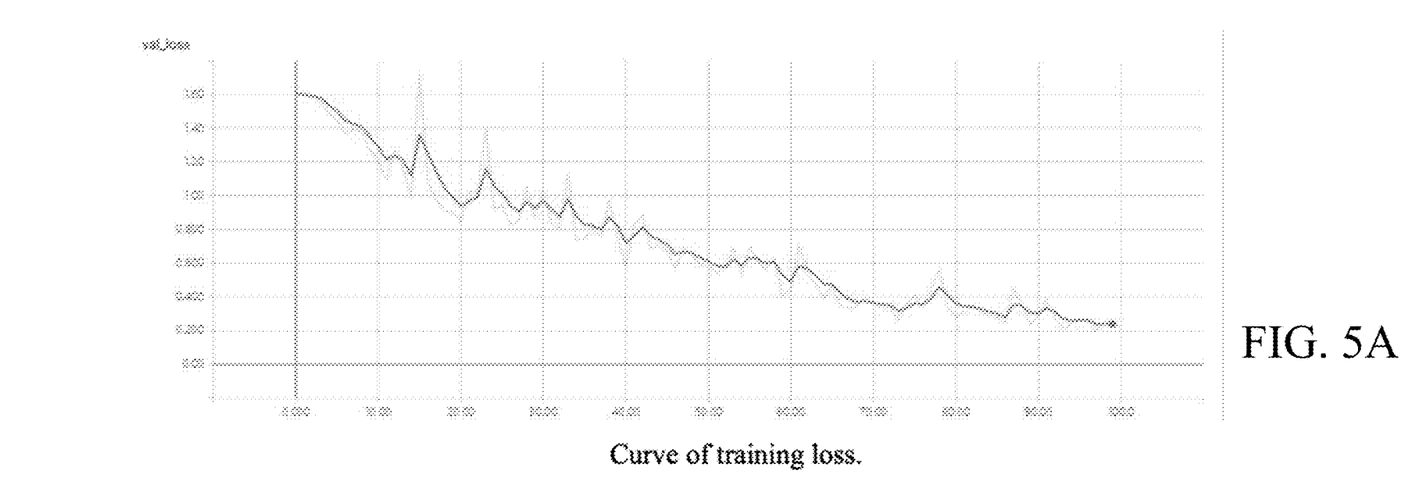
FIGS. 5A and 5B are graphs indicating better performance with great training dataset feeds.
Figure 5B:
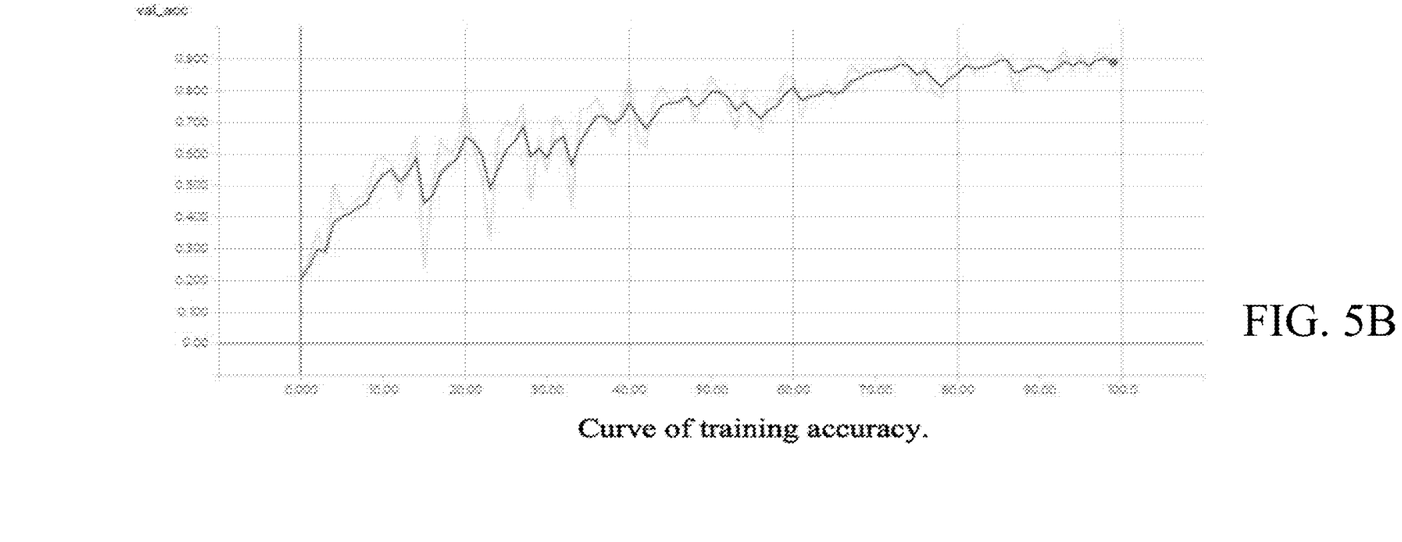

FIG. 4 is a block diagram of an example deep learning framework 4000 for posture classification in accordance with embodiments of this disclosure. As noted, extracted feature maps marked with the patient bone nodes are used as a training dataset for building a posture model and/or classifier 1322. In implementations, data enhancement can be used to expand the training dataset. The range of random rotation of images during the data enhancement is set to 20. The range of horizontal shift of images is set to 0.2 (the ratio of width before and after the shift) and images can do horizontal reversal randomly. The training dataset is categorized as training set, verification set, and testing set, which takes up 80%, 10% and 10% respectively. The constructed dataset is then used to train the posture model and/or classifier 1322 to optimize the parameters and is then stored. FIGS. 5A and 5B are graphs indicating better performance with great training dataset feeds. The graphs show the capability of the algorithm to auto-learn and auto correct as more data is fed into the framework 4000.

In implementations, the framework 4000 is a multilayer convolutional neural network (CNN) and includes a posture training segment 4100 and a classification segment 4200 where the input are the processed images having a defined pixel array size and the output is the classification. In implementations, the framework 4000 has 19 layers. The posture training segment 4100 includes convolutional layers 4110 where the input layer is for inputting the processed images having the defined pixel array size. Activation layers in the posture training segment 4100 can use rectified linear units (RELUs) 4120 and pooling layers 4130 use a defined stride. In implementations, the stride is (2,2). A stochastic gradient descent (SGD) with momentum optimizer is used for training. A categorical crossentropy is adopted as the loss function and classification labels are vectorized with One-Hot Encoding, for example, based on the number of classifications. In this instance, there are two categories so the classification labels are a 2-dimensional vector. In implementations, the classification segment 4200 can be implemented using a fully connected layer 4210 and a classifier 4220, such as a softmax classifier, for example. The framework 4000 may include other elements which may be desirable or necessary to implement the devices, systems, compositions and methods described herein. However, because such elements and steps are well known in the art, and because they do not facilitate a better understanding of the disclosed embodiments, a discussion of such elements and steps may not be provided herein.

Figure 6:
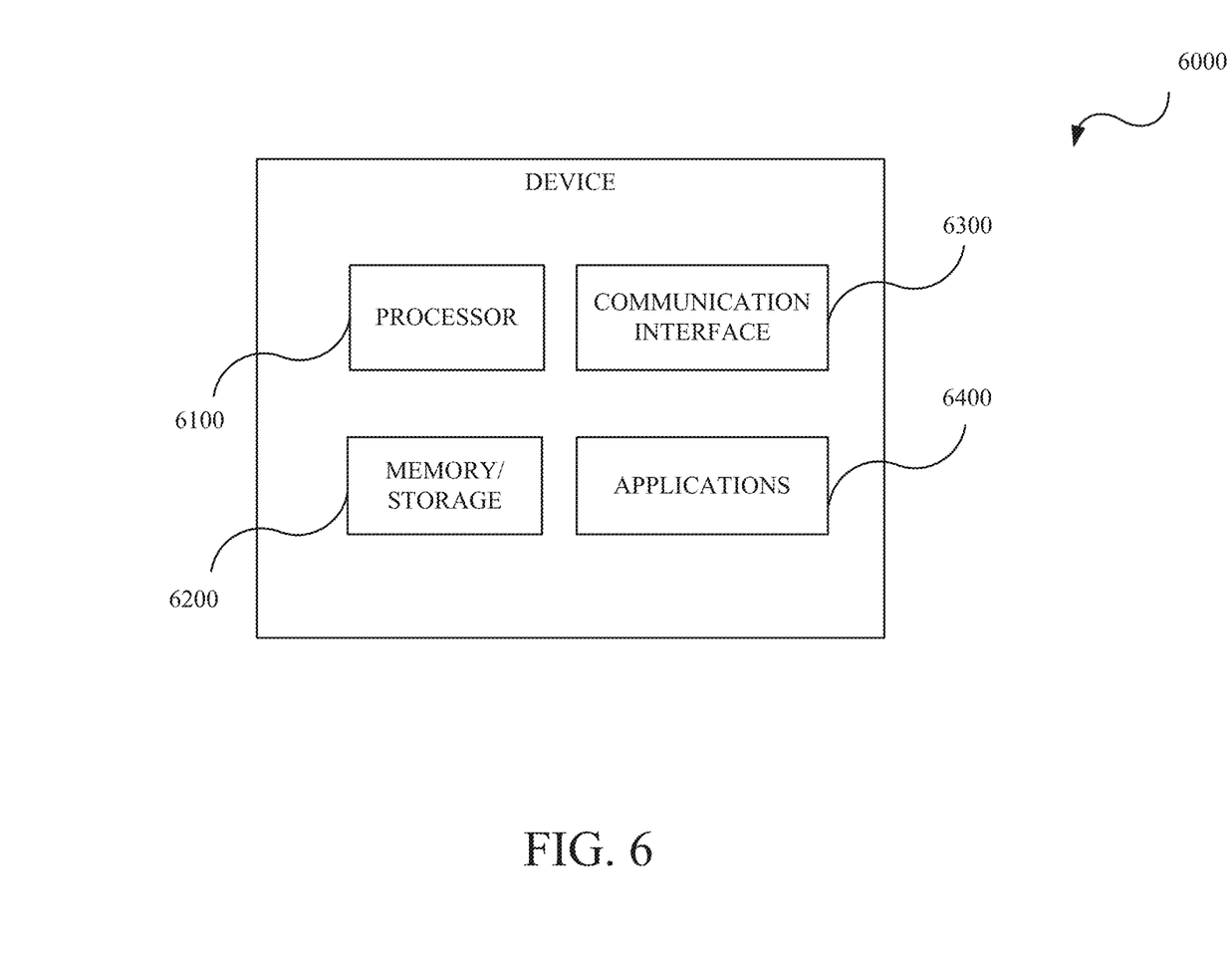
FIG. 6 is a block diagram of an example of a device in accordance with embodiments of this disclosure.

FIG. 6 is a block diagram of an example of a device 6000 in accordance with embodiments of this disclosure. The device 6000 may include, but is not limited to, a processor 6100, a memory/storage 6200, a communication interface 6300, and applications 6400. The device 6000 may include or implement, for example, the gateway or network device 1200, the edge gateway or network device 1300, the health monitoring personnel station 1400, the fall prevention unit 1310, the anonymization and posture determination unit and classifier 1320, the bedside patient monitor 1130, and the framework 4000, for example. In an implementation, appropriate memory/storage 6200 may store the sensor data and the processed image data. In an implementation, appropriate memory/storage 6200 is encoded with instructions for at least fall prevention, image anonymization, posture classifier generation, and posture detection. The instructions can further include programmed instructions for performing one or more of analysis via convolutional neural networks and deep learning analysis. The fall detection techniques or methods, the anonymization and posture determination techniques or methods, and the posture model and classification techniques or methods described herein may be stored in appropriate memory/storage 6200 and executed by the appropriate processor 6100 in cooperation with the memory/storage 6200, the communications interface 6300, and applications 6400, as appropriate. The device 6000 may include other elements which may be desirable or necessary to implement the devices, systems, compositions and methods described herein. However, because such elements and steps are well known in the art, and because they do not facilitate a better understanding of the disclosed embodiments, a discussion of such elements and steps may not be provided herein.

Figure 7:
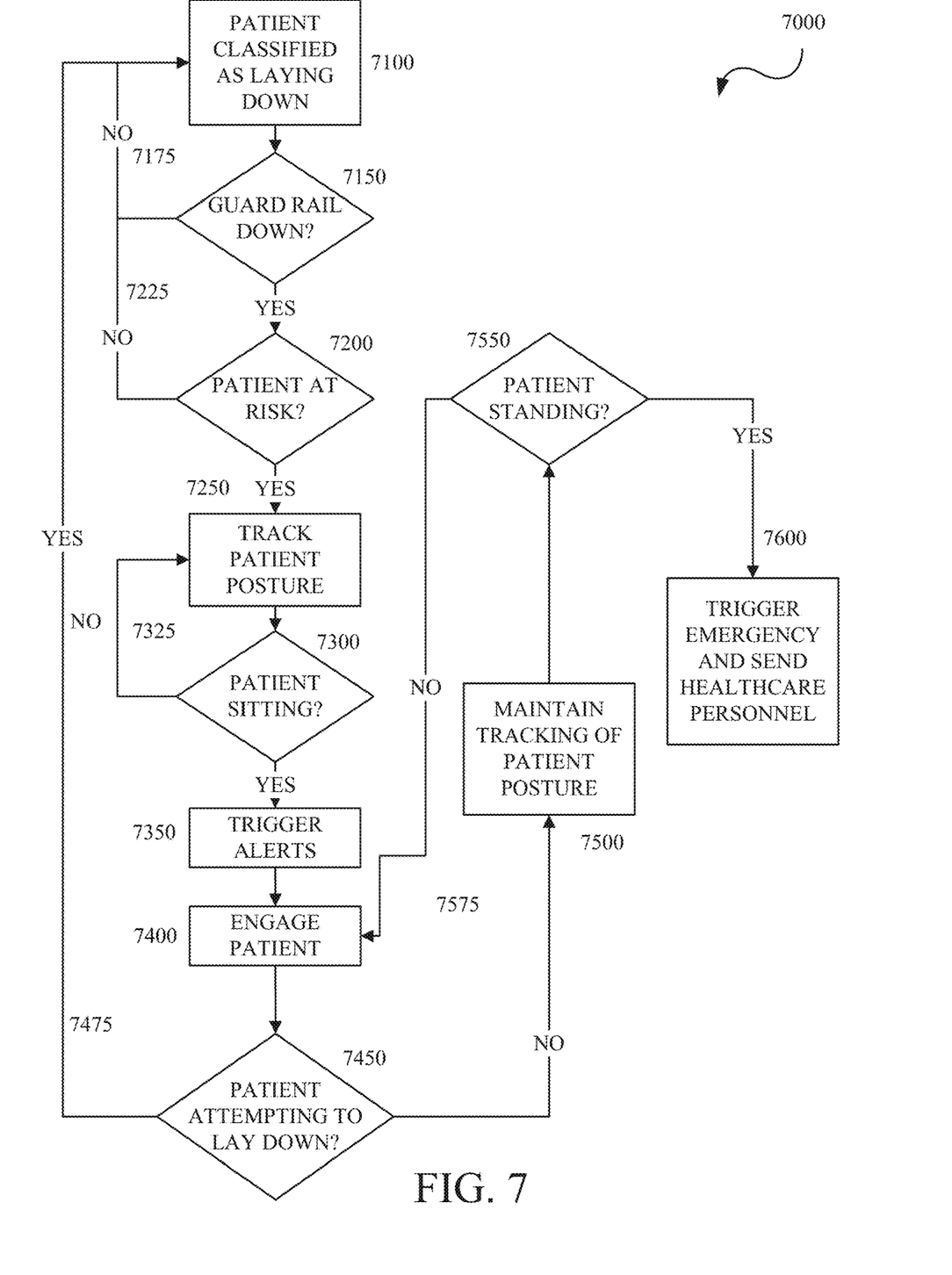
FIG. 7 is a flowchart of an example method for fall prevention in accordance with embodiments of this disclosure.

FIG. 7 is a flowchart of an example method 7000 for fall prevention in accordance with embodiments of this disclosure. The method 7000 includes: affirming 7100 that a patient is laying down on a platform; determining 7150 a guard rail status; maintaining 7175 status quo if guard rail is up; determining 7200 a health status of the patient if guard rail is down; maintaining 7225 status quo if the health status is not risky; tracking 7250 a patient posture if the health status is risky; determining 7300 if the patient is sitting; continuing 7325 tracking if patient is not sitting; triggering 7350 alerts at health monitoring station if patient is not sitting; engaging 7400 communications with patient; determining 7450 if patient is going to lay down; disengaging 7475 tracking and alerts if the patient is laying down; continuing 7500 tracking if the patient is not laying down; determining 7550 if the patient is standing; continuing 7575 communications if patient is not standing; and triggering 7600 emergency and call healthcare personnel if patient is standing. For example, the method 7000 may be implemented, as applicable and appropriate, by the architecture or system 100 of FIG. 1, the gateway or network device 1200 of FIG. 1, the edge gateway or network device 1300 of FIG. 1, the health monitoring personnel station 1400 of FIG. 1, the fall prevention unit 1310 of FIG. 1, the anonymization and posture determination unit and classifier 1320 of FIG. 1, the bedside patient monitor 1130 of FIG. 1, the framework 4000 of FIG. 4, and the processor 6100 of FIG. 6.

The method 7000 includes affirming 7100 that a patient is laying down on a platform. An initialization state upon a patient being on a platform in a room of a medical facility is that that the patient is laying on the platform. This is also the returning state if the patient had moved from this position and has now returned to the laying position.

The method 7000 includes determining 7150 a guard rail status. Platforms such as beds nominally have guard rails to prevent a patient from falling from the platform. These guard rails are provided with sensors which communicate status to a gateway and eventually a health monitoring station which is also in communication with an edge gateway in the room.

The method 7000 includes maintaining 7175 status quo if guard rail is up. No additional patient tracking is performed if the guard rail is up.

The method 7000 includes determining 7200 a health status of the patient if guard rail is down. A health status of the patient is determined. For example, the health status can be maintained and obtained from the health monitoring station, a patient bedside monitor, or combinations thereof.

The method 7000 includes maintaining 7225 status quo if the health status is not risky. No additional patient tracking is performed if the patient does not pose a risk to themselves.

The method 7000 includes tracking 7250 a patient posture if the health status is risky. A video camera in the room is triggered if the patient poses a problem to themselves. The video camera captures video and/or images of the patient and transmits the captured video and/or images to an edge gateway in the room.

The method 7000 includes determining 7300 if the patient is sitting. The edge gateway anonymizes the captured video and/or images as described herein. Skeleton images based on the captured video and/or images are constructed or generated. For example, since body posture changes will result in changes in positions of body joints, graph information within the range between the minimum and maximum coordinates of x and y will be preserved when the dataset is constructed. That is, image data that is within a defined range as determined by minimum and maximum coordinates of x and y of each body joint is preserved and other image data is deleted. The background is set to black and any redundant data is diminished. The skeleton image is downsized, normalized, and processed against a posture classifier. The posture classifier is trained as described in FIG. 8.

The method 7000 includes continuing 7325 tracking if patient is not sitting or standing. If the posture classifier predicts that the patient is still laying down, then tracking is maintained but no further action is taken. Tracking may be terminated at any moment if the patient is laying down and the guard rail is up.

The method 7000 includes triggering 7350 alerts at health monitoring station if patient is sitting. Alerts can be indicated on a dashboard at the health monitoring station if the rail is down, the patient is at risk, and the patient is sitting.

The method 7000 includes engaging 7400 communications with patient. Health personnel can engage in communications with the patient to get the patient to lay back down or determine what the issue may be.

The method 7000 includes determining 7450 if patient is going to lay down. Tracking a posture of the patient during engagement process to see if patient is being response.

The method 7000 includes disengaging 7475 tracking and alerts if the patient is laying down. Video camera and alerts are turned off. Dashboard returns to normal.

The method 7000 includes continuing 7500 tracking if the patient is not laying down. Tracking of the patient is maintained during the ongoing engagement process with the patient.

The method 7000 includes determining 7550 if the patient is standing.

The method 7000 includes continuing 7575 communications if patient is not standing. The engagement and tracking is maintained if the patient is still sitting but not standing.

The method 7000 includes triggering 7600 emergency and call healthcare personnel if patient is standing. Escalation of the alerts occurs if the patient is now standing. For example, health personnel may be alerted to go to patient's room.

Figure 8:
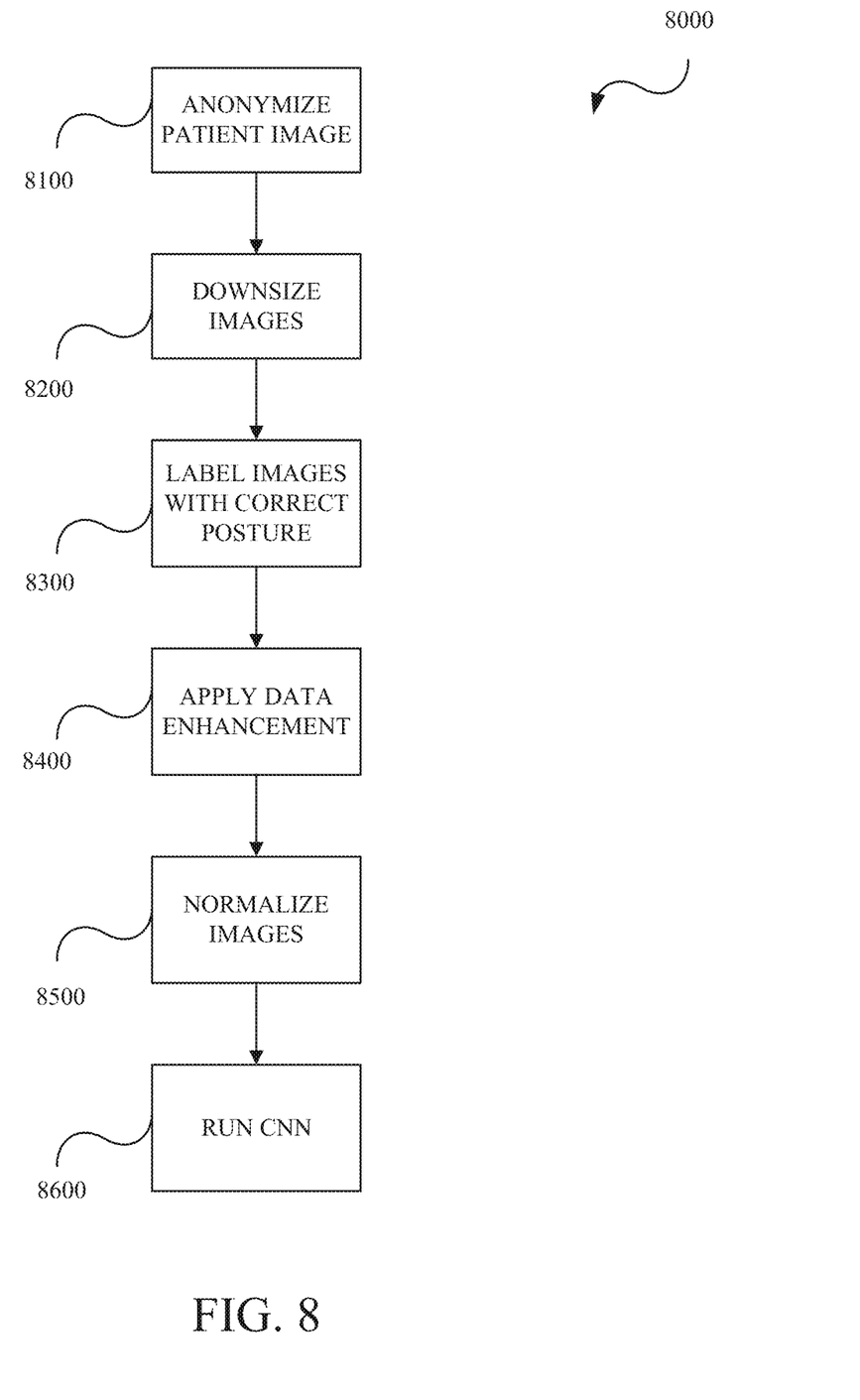
FIG. 8 is a flowchart of an example method for anonymization and posture detection training in accordance with embodiments of this disclosure.

FIG. 8 is a flowchart of an example method 8000 for anonymization and posture detection training in accordance with embodiments of this disclosure. The method 8000 includes: anonymizing 8100 patient image data; downsizing 8200 the skeleton images; labeling 8300 the skeleton images with correct postures with a defined value; applying 8400 data enhancement to the skeleton images; normalizing 8500 the skeleton images; and processing 8600 the skeleton images through the CNN to train a classifier. For example, the method 8000 may be implemented, as applicable and appropriate, by the architecture or system 100 of FIG. 1, the gateway or network device 1200 of FIG. 1, the edge gateway or network device 1300 of FIG. 1, the health monitoring personnel station 1400 of FIG. 1, the fall prevention unit 1310 of FIG. 1, the anonymization and posture determination unit and classifier 1320 of FIG. 1, the bedside patient monitor 1130 of FIG. 1, the framework 4000 of FIG. 4, and the processor 6100 of FIG. 6.

The method 8000 includes anonymizing 8100 patient image data. The captured video and/or images are anonymized by maintaining the image data relevant to determining body node changes. For example, since body posture changes will result in changes in positions of body joints, graph information within the range between the minimum and maximum coordinates of x and y will be preserved when the dataset is constructed. That is, image data that is within a defined range as determined by minimum and maximum coordinates of x and y of each body joint is preserved and other image data is deleted. In addition, the background of the image is set to black and any redundant data is diminished.

The method 8000 includes downsizing 8200 the skeleton images. The images are downsized to a defined pixel array size. Edges of the pixels are set to black.

The method 8000 includes labeling 8300 the skeleton images with correct postures with a defined value. Label images with incorrect sitting postures with a different defined value.

The method 8000 includes applying 8400 data enhancement to the skeleton images. Increase training dataset using data enhancement techniques such as rotation, for example.

The method 8000 includes normalizing 8500 the skeleton images. Each of the downsized images are normalized between a defined range.

The method 8000 includes processing 8600 the skeleton images through the CNN to train a classifier. The images are run through the CNN to train and generate a classifier or model which can predict real-time monitoring images for use, for example, in the method of FIG. 7.

In general, a system for fall prevention includes a platform configured to support a patient, the platform including rails and rail sensors, an image capturing device configured to capture images of at least the patient, a patient monitor configured for interactive communication with the patient, a health monitoring station configured to receive rail sensor data and in communication with the patient monitor, and an edge network device co-located with the platform and in communication with the health monitoring station and the image capturing device. The edge network device configured to receive image data from the image capturing device when the rail sensors indicate that the rail is down and the patient is at risk to themselves, anonymize the image data to generate a skeleton image, determine a posture associated with the skeleton image, trigger alerts at the health monitoring station when the patient is predicted to be sitting instead of lying down on the platform, and trigger escalated alerts at the health monitoring station when the patient is predicted to be standing instead of lying down on the platform. In implementations, the alerts initiate communications between the patient and healthcare personnel at the health monitoring station using the patient monitor. In implementations, the escalated alerts initiate sending healthcare personnel to check on the patient. In implementations, the edge network device configured to use a posture classifier to determine the posture. In implementations, the edge network device configured to train the posture classifier. In implementations, to train the posture classifier the edge network device is configured to anonymize training image data to generate multiple training skeleton images, downsize training skeleton images to a defined size, label downsized training skeleton images having a sitting posture as correct, apply data enhancement to the labeled training skeleton images to generate a training dataset, normalize the training dataset, and process the training dataset through a convolutional neural network to train the classifier. In implementations, for anonymization the edge network device is configured to preserve image data within a range defined by coordinates of bone nodes in the skeleton image.

In general, a method for fall prevention includes receiving image data from a camera when guard rail sensors indicate that a guard rail on a bed having an at-risk patient is down, anonymizing the image data to generate a graphical image using bone nodes, determining a posture associated with the graphical image, initiating an alert level on a dashboard at a medical personnel station when the patient is predicted to be sitting on the bed, and escalating the alert level on the dashboard at the medical personnel station when the patient is predicted to be standing. In implementations, the method includes starting the camera when the guard rail sensors indicate that the guard rail is down and there is an at-risk patient, and tracking the posture of the patient. In implementations, the anonymizing the image data further including maintaining image data within a range defined by coordinates of bone nodes in the graphical image, and setting pixels in an edge area to black. In implementations, the method includes engaging in communications with the patient by medical personnel when the alert level is initiated. In implementations, the method includes continuing tracking of the posture of the patient during communications between the medical personnel and the patient to determine patient responsiveness and reaction. In implementations, the method includes sending the medical personnel to the patient when escalating the alert level. In implementations, the determining the posture further includes using a classifier to predict the posture from the graphical image. In implementations, the using the classifier further includes anonymizing training image data to generate multiple training graphical images, downsizing training graphical images to a defined size, labeling downsized training graphical images having a sitting posture as correct, applying data enhancement to the labeled training graphical images to generate a training dataset, normalize the training dataset, and process the training dataset through a convolutional neural network to train the classifier.

In general, a system for fall prevention includes a video camera configured to capture images of a patient and a bed in a medical facility room, a monitoring station configured to receive sensor data from at least a rail sensor on the bed, a bedside monitor configured for interactive communication with the patient and between the monitoring station, and an edge gateway co-located and in communication with the video camera and the monitoring station. The edge gateway configured to generate a skeleton image by anonymizing image data received from the video camera which is activated when the rail sensor indicates that a rail sensor is disengaged and the patient has a health status of risky, classify a posture associated with the skeleton image, transmit a first alert to the monitoring station when the posture is classified as sitting, and transmit a second alert to the monitoring station when the posture is classified as standing. In implementations, wherein communications between the patient and medical personnel are initiated using the patient monitor in response to the first alert. In implementations, wherein the medical personnel are sent to the patient in response to the second alert. In implementations, for anonymization the edge network device is configured to preserve image data within a range defined by coordinates of bone nodes in the skeleton image. In implementations, to train a classifier the edge network device is configured to anonymize training image data to generate multiple training skeleton images, downsize training skeleton images to a defined size, label downsized training skeleton images having a sitting posture as correct, apply data enhancement to the labeled training skeleton images to generate a training dataset, normalize the training dataset, and process the training dataset through a convolutional neural network to train the classifier.

Although some embodiments herein refer to methods, it will be appreciated by one skilled in the art that they may also be embodied as a system or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "processor," "device," or "system." Furthermore, aspects of the present invention may take the form of a computer program product embodied in one or more the computer readable mediums having the computer readable program code embodied thereon. Any combination of one or more computer readable mediums may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to CDs, DVDs, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures.

While the disclosure has been described in connection with certain embodiments, it is to be understood that the disclosure is not to be limited to the disclosed embodiments but, on the contrary, is intended to cover various modifications, combinations, and equivalent arrangements included within the scope of the appended claims, which scope is to be accorded the broadest interpretation so as to encompass all such modifications and equivalent structures as is permitted under the law.

What is claimed is:

1. A system for fall prevention, comprising:
    a platform configured to support a patient, the platform including rails and rail sensors;
    an image capturing device configured to capture images of at least the patient;
    a patient monitor configured for interactive communication with the patient;
    a health monitoring station configured to receive rail sensor data and in communication with the patient monitor; and
    an edge network device co-located with the platform and in communication with the health monitoring station and the image capturing device, the edge network device configured to:
        receive image data from the image capturing device when the rail sensors indicate that the rail is down and the patient is at risk to themselves;
        anonymize the image data to generate a skeleton image, wherein the images of at least the patient are not stored,
            wherein to anonymize the image data includes preserving the image data relevant to determining body node changes,
            wherein preserving the image data relevant to determining body node changes includes preserving the image data within a range between the minimum and maximum coordinates of x and y of each body joint, and deleting other image data;
        train a posture classifier, wherein to train the posture classifier includes:
            anonymizing training image data to generate multiple training skeleton images;
            downsizing training skeleton images to a defined size;
            labeling downsized training skeleton images having a sitting posture as correct:
            applying data enhancement to the labeled training skeleton images to generate a training dataset;
            normalizing the training dataset; and
            processing the training dataset through a convolutional neural network to train the posture classifier;
        determine, using the posture classifier, a posture associated with the skeleton image;
        trigger alerts at the health monitoring station when the patient is predicted to be sitting instead of lying down on the platform based on the skeleton image; and
        trigger escalated alerts at the health monitoring station when the patient is predicted to be standing based on the skeleton image instead of lying down on the platform based on the skeleton image.

2. The system of claim 1, wherein the alerts initiate communications between the patient and healthcare personnel at the health monitoring station using the patient monitor.

3. The system of claim 1, wherein the escalated alerts initiate sending healthcare personnel to check on the patient.

4. A method for fall prevention, the method comprising:
    receiving image data from a camera when guard rail sensors indicate that a guard rail on a bed having an at-risk patient is down;
    anonymizing the image data to generate a graphical image using bone nodes,
        wherein the image data from the camera is not stored,
        wherein anonymizing the image data to generate the graphical image includes preserving the image data relevant to determining body node changes,
        wherein preserving the image data relevant to determining body node changes includes preserving an image portion within a range between the minimum and maximum coordinates of x and y of each body joint, and removing other image portion;
    determining a posture associated with the graphical image;
    initiating an alert level on a dashboard at a medical personnel station when the patient is predicted to be sitting on the bed based on the posture associated with the graphical image; and
    escalating the alert level on the dashboard at the medical personnel station when the patient is predicted to be standing based on the posture associated with the graphical image.

5. The method of claim 4, the method comprising:
    starting the camera when the guard rail sensors indicate that the guard rail is down and there is an at-risk patient; and
    tracking the posture of the patient.

6. The method of claim 5, wherein the anonymizing the image data further comprising:
    setting pixels in an edge area to black.

7. The method of claim 6, the method comprising:
engaging in communications with the patient by medical personnel when the alert level is initiated.

8. The method of claim 7, the method comprising:
continuing tracking of the posture of the patient during communications between the medical personnel and the patient to determine patient responsiveness and reaction.

9. The method of claim 8, the method comprising:
sending the medical personnel to the patient when escalating the alert level.

10. The method of claim 9, wherein the determining the posture further comprising:
using a classifier to predict the posture from the graphical image.

11. The method of claim 10, wherein the using the classifier further comprising:
anonymizing training image data to generate multiple training graphical images;
downsizing training graphical images to a defined size;
labeling downsized training graphical images having a sitting posture as correct;
applying data enhancement to the labeled training graphical images to generate a training dataset;
normalize the training dataset; and
process the training dataset through a convolutional neural network to train the classifier.

12. A system for fall prevention, comprising:
a video camera configured to capture images of a patient and a bed in a medical facility room;
a monitoring station configured to receive sensor data from at least a rail sensor on the bed;
a bedside monitor configured for interactive communication with the patient and between the monitoring station; and
an edge gateway co-located and in communication with the video camera and the monitoring station, the edge gateway configured to:
generate a skeleton image by anonymizing image data received from the video camera which is activated when the rail sensor indicates that a rail sensor is disengaged and the patient has a health status of risky, wherein the image data received from the video camera is not stored;
train a posture classifier, wherein to train the posture classifier includes:
anonymizing training image data to generate multiple training skeleton images;
downsizing training skeleton images to a defined size;
labeling downsized training skeleton images having a sitting posture as correct:
applying data enhancement to the labeled training skeleton images to generate a training dataset;
normalizing the training dataset; and
processing the training dataset through a convolutional neural network to train the posture classifier;
classify, using the posture classifier, a posture associated with the skeleton image;
transmit a first alert to the monitoring station when the posture is classified as sitting; and
transmit a second alert to the monitoring station when the posture is classified as standing.

13. The system of claim 12, wherein communications between the patient and medical personnel are initiated using the patient monitor in response to the first alert.

14. The system of claim 13, wherein the medical personnel are sent to the patient in response to the second alert.

15. The system of claim 12, wherein for anonymization the edge network device is configured to preserve image data within a range defined by coordinates of bone nodes in the skeleton image and foregoes transmission of the image data received from the video camera beyond the edge network device.

\* \* \* \* \*